United States Patent
Hongo et al.

(10) Patent No.: US 11,911,219 B2
(45) Date of Patent: Feb. 27, 2024

(54) ULTRASONIC DIAGNOSTIC APPARATUS AND ULTRASONIC PROBE

(71) Applicant: Konica Minolta, Inc., Tokyo (JP)

(72) Inventors: Hideo Hongo, Yokohama (JP); Takehiko Suginouchi, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 402 days.

(21) Appl. No.: 17/229,924

(22) Filed: Apr. 14, 2021

(65) Prior Publication Data

US 2021/0378637 A1   Dec. 9, 2021

(30) Foreign Application Priority Data

Jun. 4, 2020   (JP) .................... 2020-097799

(51) Int. Cl.
*A61B 8/08*   (2006.01)
*A61B 8/00*   (2006.01)

(52) U.S. Cl.
CPC .......... *A61B 8/5207* (2013.01); *A61B 8/4245* (2013.01); *A61B 8/4461* (2013.01); *A61B 8/466* (2013.01); *A61B 8/483* (2013.01); *A61B 8/54* (2013.01)

(58) Field of Classification Search
CPC ... A61B 8/5207; A61B 8/4245; A61B 8/4461; A61B 8/466; A61B 8/483; A61B 8/54
See application file for complete search history.

(56) References Cited

U.S. PATENT DOCUMENTS

| | | | | |
|---|---|---|---|---|
| 4,892,103 A | * | 1/1990 | Ogasawara | G01S 7/5206 73/620 |
| 2008/0265824 A1 | * | 10/2008 | Yim | G05B 19/404 318/632 |

FOREIGN PATENT DOCUMENTS

| | | | |
|---|---|---|---|
| JP | 62-109549 A | | 5/1987 |
| JP | 3346733 B2 | * | 11/2002 |
| JP | 2008-295958 A | | 12/2008 |
| JP | 2011-027628 A | | 2/2011 |

(Continued)

OTHER PUBLICATIONS

Translated copy Hongo JP2016016038 (Year: 2016).*

(Continued)

*Primary Examiner* — Katherine L Fernandez
*Assistant Examiner* — Brooke Lyn Klein
(74) *Attorney, Agent, or Firm* — RANKIN, HILL & CLARK LLP

(57) ABSTRACT

An ultrasonic diagnostic apparatus generates an ultrasonic image of a subject by using an ultrasonic probe, and the ultrasonic diagnostic apparatus includes: a transducer unit that is arranged in the ultrasonic probe and performs transmission and reception of ultrasonic waves; a stepping motor that is arranged in the ultrasonic probe and moves the transducer unit; a motor controller that sends a drive signal of a microstep drive method to the stepping motor; an encoder that is arranged in the ultrasonic probe, detects rotational motion of the stepping motor, and generates a detection signal having a pulse train shape depending on an amount of rotational displacement per unit time of the stepping motor; and a position data generator that generates high-resolution position data in which resolution of position data of the transducer unit obtained from the detection signal is increased.

12 Claims, 13 Drawing Sheets

(56) References Cited

FOREIGN PATENT DOCUMENTS

JP 2016016038 A * 2/2016

OTHER PUBLICATIONS

Translated copy of Shimazaki JP3346733 (Year: 2002).*
Japanese Office Action (JPOA) dated Nov. 14, 2023 for Japanese Patent Application No. 2020-097799 and its English translation.

* cited by examiner

| BEFORE CONVERSION (400 PULSES/ROTATION) | AFTER CONVERSION (500 PULSES/ROTATION) |
|---|---|
| 0 | 0 |
| 1 | 1 |
| 2 | 2 |
| 3 | 3 |
| 4 | 5 |
| 5 | 6 |
| 6 | 7 |
| 7 | 8 |
| 8 | 10 |
| 9 | 11 |
| 10 | 12 |
| 11 | 13 |
| 12 | 15 |
| 13 | 16 |
| — | — |
| — | — |
| — | — |

| POSITION DATA COUNT VALUE | POSITION DATA COUNT-UP TIMING |
|---|---|
| 5m | WHEN FOUR MICROSTEP OUTPUT PULSES ARE INPUT AFTER REFLECTION OF IMMEDIATELY PRECEDING CONVERSION ENCODER COUNT VALUE |
| 5m+1 | WHEN THREE MICROSTEP OUTPUT PULSES ARE INPUT AFTER REFLECTION OF IMMEDIATELY PRECEDING CONVERSION ENCODER COUNT VALUE |
| 5m+2 | WHEN TWO MICROSTEP OUTPUT PULSES ARE INPUT AFTER REFLECTION OF IMMEDIATELY PRECEDING CONVERSION ENCODER COUNT VALUE |
| 5m+3 | WHEN ONE MICROSTEP OUTPUT PULSE IS INPUT AFTER REFLECTION OF IMMEDIATELY PRECEDING CONVERSION ENCODER COUNT VALUE |
| 5m+4 | WHEN PULSE OF DETECTION SIGNAL OF ENCODER IS INPUT |

| BEFORE CONVERSION (400 PULSES/ROTATION) | AFTER CONVERSION (1000 PULSES/ROTATION) |
|---|---|
| 0 | 0 |
| 1 | 2 |
| 2 | 5 |
| 3 | 7 |
| 4 | 10 |
| 5 | 12 |
| 6 | 15 |
| 7 | 17 |
| 8 | 20 |
| 9 | 22 |
| 10 | 25 |
| 11 | 27 |
| 12 | 30 |
| 13 | 32 |
| — | — |
| — | — |
| — | — |

| POSITION DATA COUNT VALUE | POSITION DATA COUNT-UP TIMING |
|---|---|
| 10m | WHEN TWO MICROSTEP OUTPUT PULSES ARE INPUT AFTER REFLECTION OF IMMEDIATELY PRECEDING CONVERSION ENCODER COUNT VALUE |
| 10m+1 | WHEN FOUR MICROSTEP OUTPUT PULSES ARE INPUT AFTER REFLECTION OF IMMEDIATELY PRECEDING CONVERSION ENCODER COUNT VALUE |
| 10m+2 | WHEN ONE MICROSTEP OUTPUT PULSE IS INPUT AFTER REFLECTION OF IMMEDIATELY PRECEDING CONVERSION ENCODER COUNT VALUE |
| 10m+3 | WHEN THREE MICROSTEP OUTPUT PULSES ARE INPUT AFTER REFLECTION OF IMMEDIATELY PRECEDING CONVERSION ENCODER COUNT VALUE |
| 10m+4 | WHEN PULSE OF DETECTION SIGNAL OF ENCODER IS INPUT |
| 10m+5 | WHEN TWO MICROSTEP OUTPUT PULSES ARE INPUT AFTER REFLECTION OF IMMEDIATELY PRECEDING CONVERSION ENCODER COUNT VALUE |
| 10m+6 | WHEN FOUR MICROSTEP OUTPUT PULSES ARE INPUT AFTER REFLECTION OF IMMEDIATELY PRECEDING CONVERSION ENCODER COUNT VALUE |
| 10m+7 | WHEN ONE MICROSTEP OUTPUT PULSE IS INPUT AFTER REFLECTION OF IMMEDIATELY PRECEDING CONVERSION ENCODER COUNT VALUE |
| 10m+8 | WHEN THREE MICROSTEP OUTPUT PULSES ARE INPUT AFTER REFLECTION OF IMMEDIATELY PRECEDING CONVERSION ENCODER COUNT VALUE |
| 10m+9 | WHEN PULSE OF DETECTION SIGNAL OF ENCODER IS INPUT |

ULTRASONIC DIAGNOSTIC APPARATUS AND ULTRASONIC PROBE

The entire disclosure of Japanese patent Application No. 2020-097799, filed on Jun. 4, 2020, is incorporated herein by reference in its entirety.

BACKGROUND

Technological Field

The present disclosure relates to an ultrasonic diagnostic apparatus and an ultrasonic probe.

Description of the Related Art

An ultrasonic diagnostic apparatus has conventionally been known that generates an ultrasonic image of a subject by transmitting ultrasonic waves into the subject and receiving an ultrasonic echo reflected in the subject by using an ultrasonic probe.

As an ultrasonic beam scanning method in this type of ultrasonic diagnostic apparatus, there are an electronic scanning type and a mechanical scanning type. An electronic scanning type ultrasonic diagnostic apparatus performs ultrasonic beam scanning by, for example, electrically controlling each of transducers in a transducer array. Furthermore, a mechanical scanning type ultrasonic diagnostic apparatus performs ultrasonic beam scanning by, for example, mechanically rotating a single plate-like transducer. Since the electronic scanning type ultrasonic diagnostic apparatus electrically forms an ultrasonic beam, it has an advantage that the degree of freedom is high in the beam formation position, direction, and time. On the other hand, since the mechanical scanning type ultrasonic diagnostic apparatus performs ultrasonic beam scanning mechanically, the apparatus configuration can be made simple although the degree of freedom in the beam formation position, direction, and time is considerably lower than that of the electronic type, so that the mechanical scanning type is often used as a small and inexpensive ultrasonic diagnostic apparatus.

Moreover, in recent years, development has been promoted of an ultrasonic diagnostic apparatus using both an electronic scanning type and a mechanical scanning type. In this type of ultrasonic diagnostic apparatus, an ultrasonic probe called a 4D probe is used, and a motor (typically, a stepping motor) is used to reciprocate (swing) a transducer unit provided with a transducer array in a direction orthogonal to an arrangement direction of the transducers, whereby processing of acquiring a tomographic image at each of swing positions is performed. Then, this type of ultrasonic diagnostic apparatus updates a three-dimensional image generated in this way in real time. As a result, it becomes possible for an operator to easily know a three-dimensional shape and a positional relationship of an inspection target, which has been difficult to understand in a two-dimensional image.

By the way, in the mechanical scanning type ultrasonic diagnostic apparatus, to generate a higher definition ultrasonic image, it is necessary to grasp a position of the transducer unit with higher accuracy. From such a background, in this type of ultrasonic diagnostic apparatus, a technique has been conventionally used for specifying the position of the transducer unit by detecting a rotational position of a motor for moving the transducer unit by using an encoder.

However, when an attempt is made to use a high-resolution encoder, there is a problem that the size of the encoder is increased and the size of the ultrasonic probe itself that houses the motor and the encoder is increased.

From such a background, for example, in JP 62-109549 A, a technology is disclosed for calculating current position information of the transducer unit by sequentially measuring a pulse period of the encoder and using a divided pulse obtained by dividing a pulse period immediately before into m to obtain position information of the transducer unit with higher resolution.

The conventional technology according to JP 62-109549 A is an effective method in a mode in which the motor rotates at a constant speed. However, when operation of the motor includes an acceleration/deceleration area, the pulse period always changes in the acceleration/deceleration area, so that in the conventional technology according to JP 62-109549 A, it is not possible to improve the resolution of the position information of the transducer unit obtained from a detection signal of the encoder. In particular, like the 4D probe, when swing operation of the transducer unit is performed, the acceleration/deceleration area is included in the swing operation, so that in the conventional technology according to JP 62-109549 A, it is not possible to obtain the position information of the transducer unit with high accuracy.

SUMMARY

The present disclosure has been made in view of the above problems, and it is an object to provide an ultrasonic diagnostic apparatus and an ultrasonic probe capable of increasing the resolution of the position information of the transducer unit without changing a detection resolution itself of the encoder.

To achieve the abovementioned object, according to an aspect of the present invention, there is provided an ultrasonic diagnostic apparatus that generates an ultrasonic image of a subject by using an ultrasonic probe, and the ultrasonic diagnostic apparatus reflecting one aspect of the present invention comprises: a transducer unit that is arranged in the ultrasonic probe and performs transmission and reception of ultrasonic waves; a stepping motor that is arranged in the ultrasonic probe and moves the transducer unit; a motor controller that sends a drive signal of a microstep drive method to the stepping motor; an encoder that is arranged in the ultrasonic probe, detects rotational motion of the stepping motor, and generates a detection signal having a pulse train shape depending on an amount of rotational displacement per unit time of the stepping motor; and a position data generator that generates high-resolution position data in which resolution of position data of the transducer unit obtained from the detection signal is increased, by detecting a rise or fall of a pulse of the detection signal and detecting a rise or fall of a microstep of the drive signal when the stepping motor rotates, and by interpolating a timing between pulses of the detection signal with a number of microsteps of the drive signal as a reference.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 6 is a diagram illustrating an example of a conversion table when high-resolution position data equivalent to 500 pulses/rotation is generated from a detection signal of an encoder having a detection resolution of 400 pulses/rotation;

FIG. 7 is a diagram illustrating an example of a count processing setting table when the high-resolution position data equivalent to 500 pulses/rotation is generated from the detection signal of the encoder having the detection resolution of 400 pulses/rotation;

FIG. 11 is a diagram illustrating an example of a conversion table when high-resolution position data equivalent to 1000 pulses/rotation is generated from the detection signal of the encoder having the detection resolution of 400 pulses/rotation;

FIG. 12 is a diagram illustrating an example of the count processing setting table when the high-resolution position data equivalent to 1000 pulses/rotation is generated from the detection signal of the encoder having the detection resolution of 400 pulses/rotation.

DETAILED DESCRIPTION OF EMBODIMENTS

Figure 1:
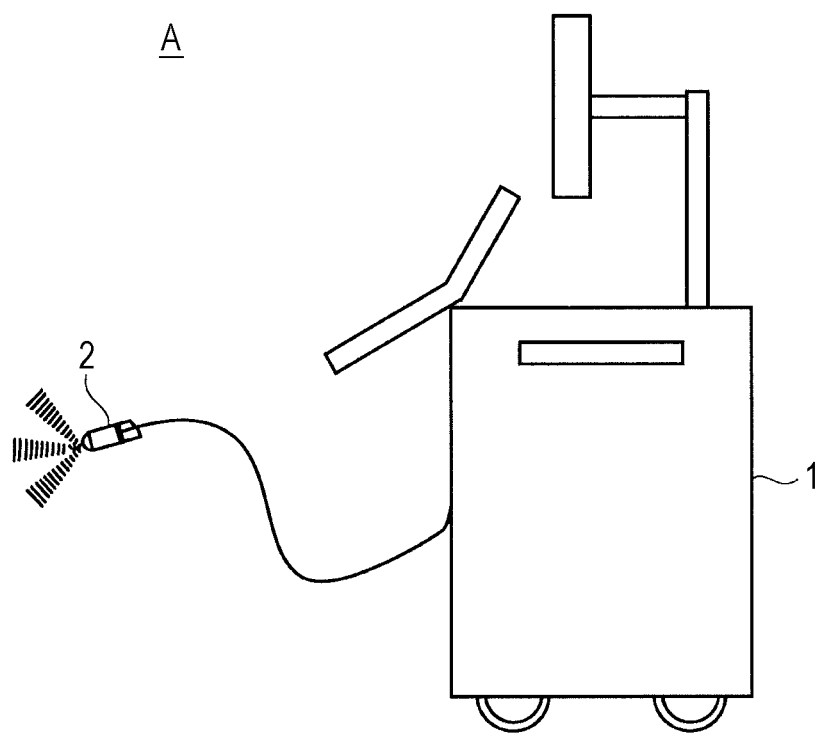
FIG. 1 is a diagram illustrating an example of an appearance of an ultrasonic diagnostic apparatus.

Hereinafter, one or more embodiments of the present invention will be described with reference to the drawings. However, the scope of the invention is not limited to the disclosed embodiments. Note that, in the present specification and the drawings, components having substantially the same function will be denoted by the same reference numerals, and redundant descriptions will be omitted.

[Configuration of Ultrasonic Diagnostic Apparatus]

Figure 2:
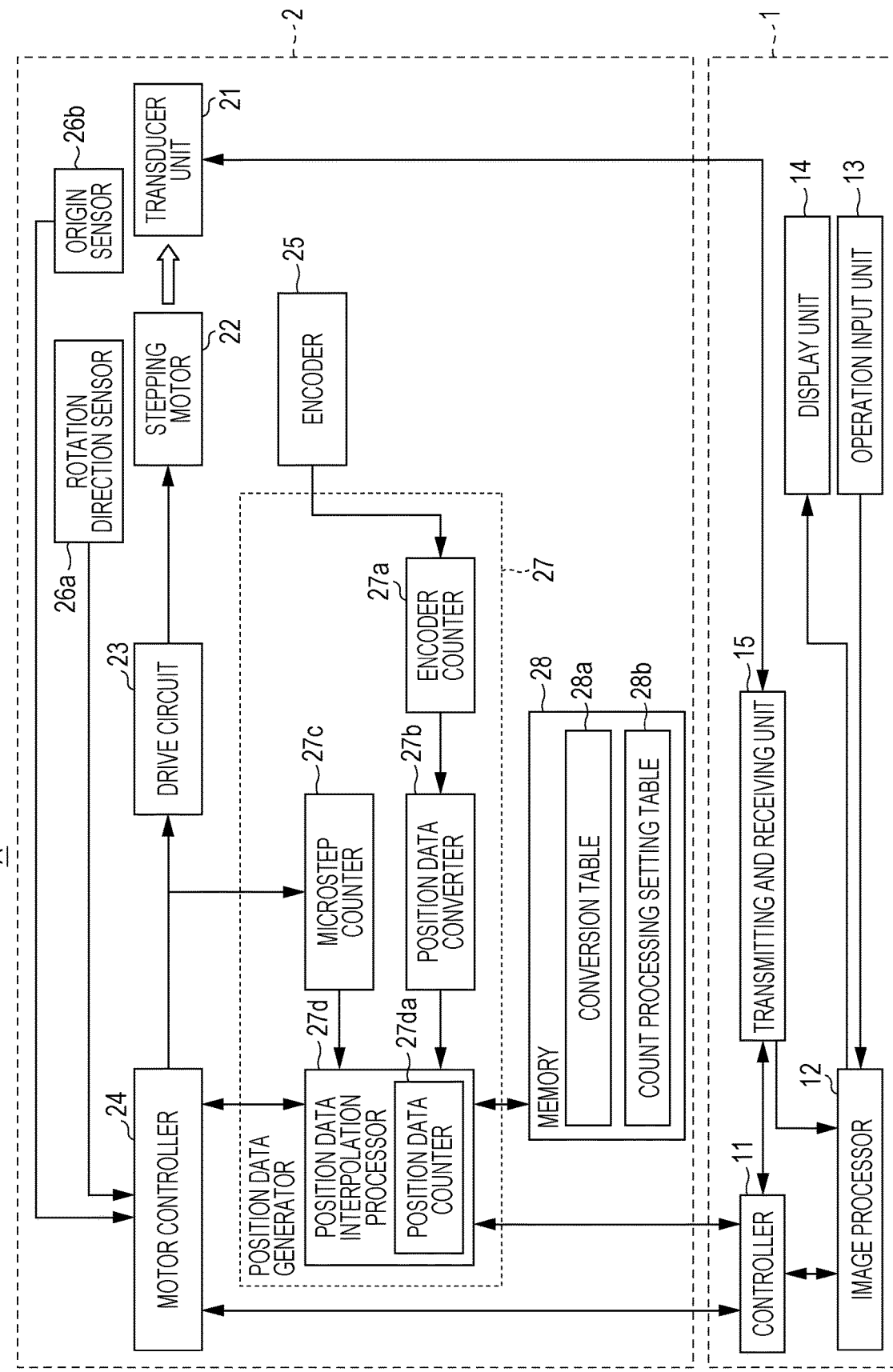
FIG. 2 is a block diagram illustrating an example of a functional configuration of an ultrasonic diagnostic apparatus.

FIG. 1 is a diagram illustrating an appearance of an ultrasonic diagnostic apparatus A according to the present embodiment. FIG. 2 is a block diagram illustrating a functional configuration of the ultrasonic diagnostic apparatus A according to the present embodiment.

In the ultrasonic diagnostic apparatus A, an ultrasonic probe 2 is attached to a main body 1 of the ultrasonic diagnostic apparatus A. The main body 1 and the ultrasonic probe 2 are electrically connected together via a cable C. Note that, in the present embodiment, a 4D probe is used as the ultrasonic probe 2.

The main body 1 includes a controller 11, an image processor 12, an operation input unit 13, a display unit 14, and a transmitting and receiving unit 15.

The controller 11 controls overall operation of the ultrasonic diagnostic apparatus A. The controller 11 controls, for example, the transmitting and receiving unit 15 to output an ultrasonic beam from a transducer unit 21 of the ultrasonic probe 2 or to perform reception processing of an ultrasonic signal generated by the transducer unit 21. Note that, the controller 11 is, for example, a microprocessor including a Central Processing Unit (CPU), a Read Only Memory (ROM), a Random Access Memory (RAM), an input port, an output port, and the like.

Furthermore, the controller 11 outputs a control signal to a motor controller 24 of the ultrasonic probe 2 so that the transducer unit 21 performs swing operation in a predetermined mode (speed, swing range, and the like), for example. Then, for example, when the transducer unit 21 is at each of swing positions, the controller 11 performs ultrasonic scanning of the inside of a subject by sequentially driving a plurality of transducers arranged in an array shape provided in the transducer unit 21 from one side to the other side. Furthermore, the controller 11 acquires, for example, position information (high-resolution position data described later) of the transducer unit 21 from a position data interpolation processor 27d and transfers the position information to the image processor 12.

The image processor 12 generates an ultrasonic image on the basis of the ultrasonic signal received by the transducer unit 21 and acquired from the transmitting and receiving unit 15. The image processor 12 generates a three-dimensional ultrasonic image by synthesizing two-dimensional frame data (that is, tomographic image data) acquired when the transducer unit 21 is at respective swing positions on the basis of the position information of the transducer unit 21 when the frame data is acquired. Since content of processing for generating the ultrasonic image is known, description thereof is omitted here.

The operation input unit 13 receives input operation of an operator and outputs an input signal corresponding to the input operation to the image processor 12. The operation input unit 13 includes, for example, a push button switch, a keyboard, a mouse or a trackball, or a combination thereof. Alternatively, the operation input unit 13 may include a touch sensor in addition to or instead of the above configuration, detect touch operation on a display screen of the display unit 14, and output an operation signal related to an operation type and a position.

The display unit 14 includes a display screen using any of various display methods, such as a Liquid Crystal Display (LCD), an organic Electro-Luminescent (EL) display, an inorganic EL display, a plasma display, and a Cathode Ray Tube (CRT) display, and a drive unit of the display screen. The display unit 14 generates a drive signal for the display screen (each of display pixels) in accordance with the control signal output from the controller 11 and the image data generated by the image processor 12, and displays a menu and a status related to ultrasonic diagnosis, and measurement data based on received ultrasonic waves on the display screen. Furthermore, one or a plurality of lamps (LED lamps or the like) is provided, and it is possible to display a power on/off state and the like by a lighting state.

The transmitting and receiving unit 15 outputs a drive signal for causing each transducer in the transducer unit 21 to perform scanning on the basis of the control of the controller 11, sequentially generating and emitting (transmitting) ultrasonic waves to a desired transducer, and acquires an electric signal related to (received) ultrasonic waves entering the transducer. The transmitting and receiving unit 15 performs various types of processing, for example, adjusting a pulse width of the drive signal, and adjusting and delaying a timing of transmitting and receiving the ultrasonic waves for each transducer. Furthermore, the transmitting and receiving unit 15 amplifies a received signal and performs digital conversion on the signal at a predetermined sampling frequency, and also performs processing of delaying the signal by a desired timing for each transducer to perform phasing and addition, and the like.

The ultrasonic probe 2 includes the transducer unit 21, a stepping motor 22, a drive circuit 23, the motor controller 24, an encoder 25, a rotation direction sensor 26a, an origin sensor 26b, a position data generator 27, and a memory 28. Note that, these are housed in a housing of the ultrasonic probe 2.

Figure 3A:
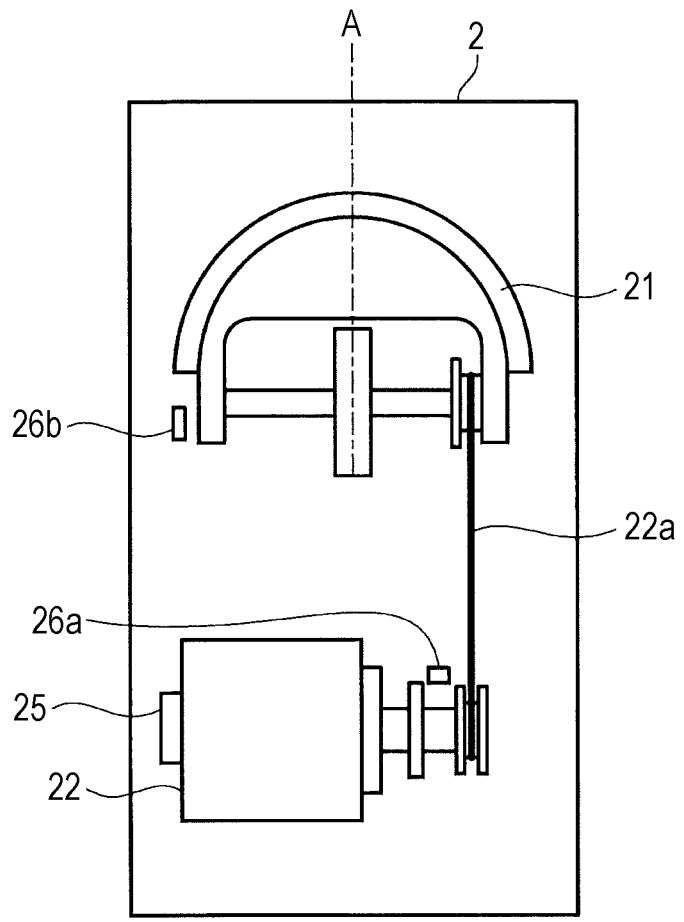
FIG. 3A is a schematic diagram illustrating an example of an internal structure of an ultrasonic probe.
Figure 3B:
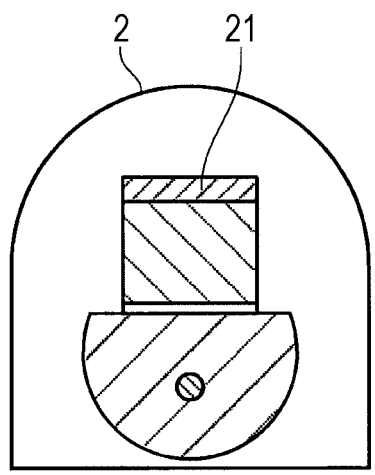
FIG. 3B is a schematic diagram illustrating an example of the internal structure of the ultrasonic probe.

FIGS. 3A and 3B are schematic diagrams illustrating an internal structure of the ultrasonic probe 2 according to the present embodiment. FIG. 3A illustrates a side sectional view of the ultrasonic probe 2, and FIG. 3B illustrates a sectional view of the front side of the ultrasonic probe 2 cut along a sectional line A in FIG. 3A.

The transducer unit 21 is, for example, one in which a plurality of transducers arranged in an array shape is fixed. Each transducer of the transducer unit 21 is, for example, a piezoelectric element that performs mutual conversion between an ultrasonic wave and an electric signal. Each transducer of the transducer unit 21 is electrically connected to the transmitting and receiving unit 15, converts a transmission signal from the transmitting and receiving unit 15 into ultrasonic waves to transmit the ultrasonic waves into the subject, and converts an ultrasonic echo reflected in the subject into an electric signal to send the electric signal to the transmitting and receiving unit 15.

The transducer unit 21 is swingably supported in the ultrasonic probe 2. The transducer unit 21 is arranged to be able to perform swing operation in an arc shape to reciprocate within a predetermined angular range in a direction orthogonal to an arrangement direction of the transducers and in a direction orthogonal to a transmission and reception direction of the ultrasonic waves depending on rotation operation of the stepping motor 22, and change an oriented direction related to the transmission and reception of the ultrasonic waves. Here, the transducer unit 21 is connected to the rotating shaft of the stepping motor 22 via a pulley mechanism 22a (see FIGS. 3A and 3B), and swings along with rotational movement of the stepping motor 22.

The stepping motor 22 is caused to perform microstep drive by a pulse-like drive signal from the motor controller 24, and swings the transducer unit 21. The type of the stepping motor 22 is arbitrary, such as a permanent magnet type (PM type), a gear-shaped iron core type (VR type), or a hybrid type (HB type), but in the present embodiment, for example, a hybrid type (HB type) stepping motor is used including a stator provided with a magnetic pole and a magnetized rotor.

Note that, the basic step of the stepping motor 22 is determined by the number of magnetic poles and the number of phases of the stepping motor 22, and in the present embodiment, the stepping motor 22 having a basic step of 1.8 degrees is used.

The drive signal output from the motor controller 24 is input to the drive circuit 23, and the drive circuit 23 generates motor drive power (or a drive current subjected to constant current control by the drive signal) by the drive signal, and sends the motor drive power to the stepping motor 22.

The motor controller 24 sends the drive signal to the stepping motor 22 via the drive circuit 23 to drive the stepping motor 22. The motor controller 24 rotates the rotor stepwise by sequentially exciting a plurality of magnetic poles provided in the stator of the stepping motor 22 by, for example, the pulse-like drive signal.

The motor controller 24 determines a mode (that is, a speed at which the transducer unit 21 is swung, and a range in which the transducer unit 21 is swung, or the like) for causing the stepping motor 22 to perform the rotation operation on the basis of the control signal from the controller 11 of an ultrasonic diagnostic apparatus main body 1, for example. At this time, the motor controller 24 identifies a rotation center position of the stepping motor 22 on the basis of detection signals from the encoder 25 and the origin sensor 26b, and determines a range in which the stepping motor 22 is rotated. Furthermore, the motor controller 24 performs data communication with the position data generator 27, and notifies the position data generator 27 of information related to the rotation center position of the stepping motor 22, information related to a rotation direction of the stepping motor 22, and the like.

Here, the motor controller 24 drives the stepping motor 22 by a microstep drive method. Microstep drive is a drive method for controlling a rotational position of the rotor of the stepping motor 22 (hereinafter, also simply referred to as "rotational position of the stepping motor 22") with higher accuracy by finely changing (for example, changing in a sinusoidal shape) the magnitude of an excitation current caused to flow through the magnetic poles of each phase of the stepping motor 22.

Figure 4:
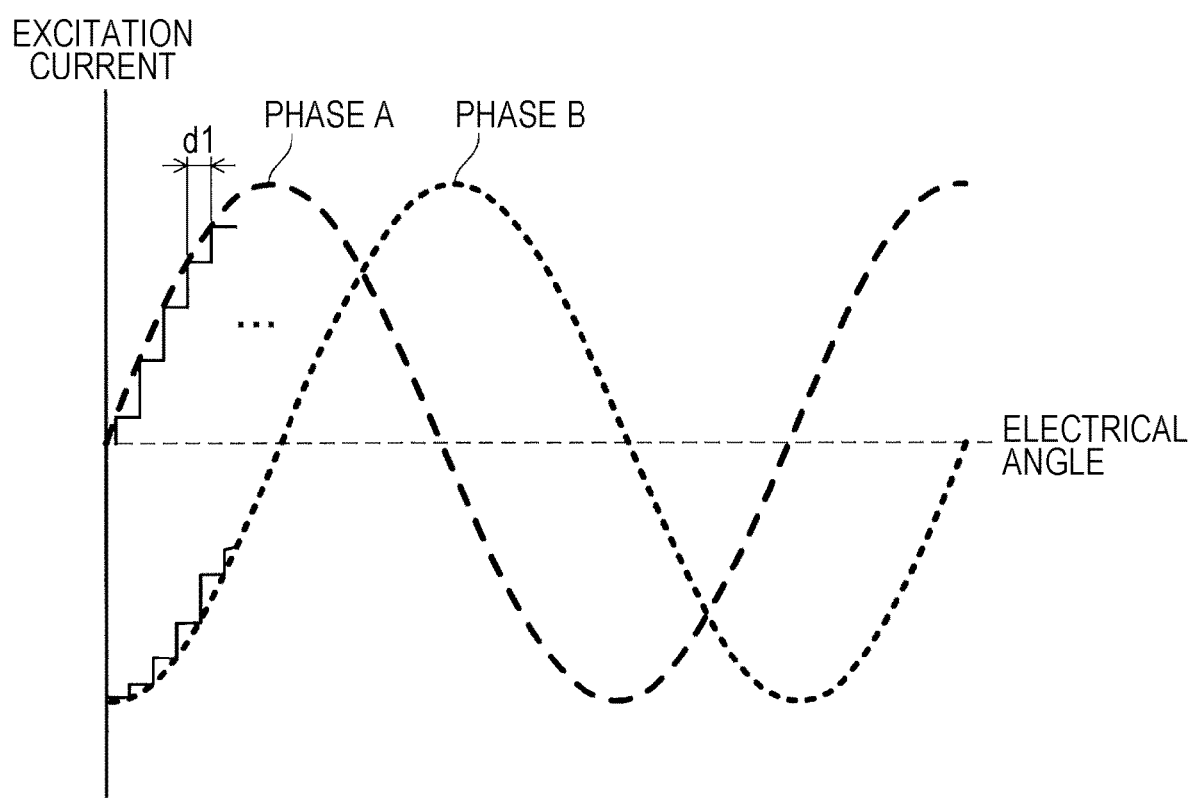
FIG. 4 is a diagram illustrating an example of a waveform of a drive signal (excitation current) for causing a stepping motor to perform microstep drive.

FIG. 4 is a diagram illustrating an example of a waveform of a drive signal (excitation current) for causing the stepping motor 22 to perform microstep drive. In FIG. 4, a mode is illustrated in which a two-phase stepping motor 22 is assumed, the magnitude of an excitation current of a drive signal having a pulse train shape (hereinafter referred to as "microstep output pulse") output to each of a phase-A magnetic pole and a phase-B magnetic pole is changed with time, and the drive signal for each basic step is made into a sinusoidal waveform.

For example, as illustrated in FIG. 4, the motor controller 24 changes the magnitude of the excitation current in microstep units obtained by dividing the basic steps of the stepping motor 22 into a predetermined number, and causes the rotor of the stepping motor 22 to rotate in the normal rotation direction or in the reverse rotation direction (that is, to perform step operation). In the present embodiment, the motor controller 24 causes the rotor of the stepping motor 22 to perform step operation by, for example, microsteps in units of 0.045 degrees obtained by further dividing the basic step 1.8 degrees of the stepping motor 22 into 40. Note that, d1 in FIG. 4 corresponds to a unit microstep.

In the present embodiment, when the motor controller 24 causes the stepping motor 22 to perform microstep drive, stepped rises or falls in microstep units in the drive signal of the mode illustrated in FIG. 4 are also collectively referred to as "rise or fall of the microstep".

Macroscopically, the rotational position of the rotor of the stepping motor 22 can be estimated only from the drive signal output from the motor controller 24. However, microscopically, the rotational position of the rotor of the stepping motor 22 may deviate from an original target rotational position by the drive signal due to a load fluctuation and the like. This is because the load fluctuation of the stepping motor 22 may occur due to the acceleration/deceleration of the transducer unit 21 during the swing operation and may cause a delay in the rotation operation of the rotor of the stepping motor 22. Furthermore, even in the case of the microstep drive, rotational power applied by a magnetic field generated by the magnetic pole of the stepping motor 22 to the rotor of the stepping motor 22 has an angle error for each microstep, and a rotation angle for each microstep may not be uniform. From this viewpoint, in the present embodiment, the encoder 25 detects the rotational position of the rotor of the stepping motor 22.

The encoder 25 detects rotational motion of the stepping motor 22, and generates a detection signal having a pulse train shape depending on an amount of rotational displacement of the stepping motor 22 per unit time. A pulse output from the encoder 25 is emitted at each predetermined rotation angle of the stepping motor 22. The encoder 25 according to the present embodiment outputs, for example, 400 pulses per rotation of the stepping motor 22.

In the present embodiment, for example, an optical encoder 25 is used as the encoder 25. The encoder 25 includes, for example, a slit disk that is attached to the rotating shaft of the rotor of the stepping motor 22 and in which a plurality of slits is carved at equal intervals in the circumferential direction, and a light emitting element and a light receiving element arranged to face each other sandwiching the slits of the slit disk. Then, for example, when the slit disk rotates along with rotational movement of the stepping motor 22, the encoder 25 detects the amount of rotational displacement of the stepping motor 22 per unit time from the pulse train generated by the light receiving element due to light and shade of light.

Note that, the encoder 25 according to the present embodiment is an optical encoder, and a phase-B output waveform is output with a ¼ period deviation from a phase-A output waveform (hereinafter, the phase-A output waveform and the phase-B output waveform are also referred to as "phase-A pulse" and "phase-B pulse").

The origin sensor 26b detects that the swing position of the transducer unit 21 (or the rotational position of the stepping motor 22) is at an origin position. A configuration of the origin sensor 26b is arbitrary, but as the origin sensor 26b, for example, a magnetic sensor or a photo sensor is used. Note that, the origin position of the swing position of the transducer unit 21 is, for example, a position corresponding to the center position of an angular range in which the swing position of the transducer unit 21 is movable.

The rotation direction sensor 26a is a sensor that detects the rotation direction of the stepping motor 22, and includes, for example, a semicircular slit plate and a photo sensor. Note that, when detecting the origin position of the swing position of the transducer unit 21, the motor controller 24 first determines whether the stepping motor 22 moves to the left or right on the basis of the detection signal of the rotation direction sensor 26a, and then specifies the origin position of the swing position of the transducer unit 21 by referring to the detection signals of the encoder 25 and the origin sensor 26b.

The position data generator 27 detects a rise or fall of the pulse of the detection signal output from the encoder 25, and also detects the rise or fall of the microstep of the drive signal output from the motor controller 24. Then, the position data generator 27 interpolates a timing between pulses of the detection signal output from the encoder 25 when the stepping motor 22 rotates, with the number of microsteps of the drive signal output from the motor controller 24 as a reference, thereby generating high-resolution position data in which resolution of the position data of the transducer unit 21 obtained from the detection signal of the encoder 25 is increased. At this time, the position data generator 27 interpolates the timing between the pulses of the detection signal on the basis of, for example, the number of microsteps of the drive signal after the rise or fall of the pulse of the detection signal immediately before is detected.

The position data generator 27 includes an encoder counter 27a, a position data converter 27b, a microstep counter 27c, and a position data interpolation processor 27d. Note that, an example of operation of the position data generator 27 will be described later with reference to FIGS. 5 to 9.

The encoder counter 27a acquires the detection signal output from the encoder 25 and generates a count value (hereinafter, referred to as "encoder count value") indicating the rotational position of the stepping motor 22 (that is, the swing position of the transducer unit 21). The encoder counter 27a is an incremental counter, for example, and performs up-counting each time the rise or fall of the pulse of the detection signal is detected. The encoder counter 27a according to the present embodiment performs up-counting each time the rise and fall of each of the phase-A pulse and the phase-B pulse are detected.

The position data converter 27b acquires the encoder count value output from the encoder counter 27a, and converts the encoder count value indicated by the encoder counter 27a to a count value (hereinafter referred to as "conversion encoder count value") with a target resolution of the high-resolution position data as a reference by using a conversion table 28a (see FIG. 6 described later) stored in the memory 28.

The microstep counter 27c acquires the drive signal output from the motor controller 24, and performs count processing for each rise or fall of the microstep of the drive signal. The microstep counter 27c according to the present embodiment generates a count value indicating the number of inputs of the microstep output pulse of the drive signal. The microstep counter 27c is an incremental counter, for example, and performs up-counting each time a rise timing of the microstep output pulse of the drive signal is detected.

The position data interpolation processor 27d acquires the conversion encoder count value output from the position data converter 27b and the count value output from the microstep counter 27c, and on the basis of these, generates the high-resolution position data. At this time, the position data interpolation processor 27d generates the high-resolution position data so that a value between conversion encoder count values output from the position data converter 27b is interpolated with the number of microsteps of the drive signal (here, the number of microstep output pulses of the drive signal) as a reference. In other words, the position data interpolation processor 27d generates the high-resolution position data by using the conversion encoder count value output from the position data converter 27b as it is, for the rotational position that can be detected from the pulse of the detection signal of the encoder 25. On the other hand, for the rotational position that cannot be detected from the pulse of the detection signal of the encoder 25, the high-resolution position data is generated from the number of microsteps of the drive signal output from the motor controller 24 (that is, the count value output from the microstep counter 27c).

More specifically, the position data interpolation processor 27d includes a position data counter 27da that generates a count value (hereinafter, referred to as "position data count value") representing the high-resolution position data. Then, the position data interpolation processor 27*d* causes the position data counter 27*da* to perform counting up as the number of microsteps of the drive signal reaches a predetermined number, and, as the position data converter 27*b* counts up the conversion encoder count value, overwrites and updates the conversion encoder count value onto the position data count value of the position data counter 27*da*.

In other words, the position data interpolation processor 27*d* uses the detection signal of the encoder 25 as a true value for specifying a position of the transducer unit 21, and refers to the number of microstep output pulses of the drive signal only for interpolating a value of resolution that cannot be obtained from the detection signal of the encoder.

Note that, to implement such operation, the position data interpolation processor 27*d* refers to a count processing setting table 28*b* (see FIG. 7 described later) stored in the memory 28 when a rise or fall of the microstep output pulse of the drive signal is detected, to determine whether or not a detected rise or fall timing corresponds to a timing for causing the position data count value to be counted up. Then, the position data interpolation processor 27*d* causes the position data count value to be counted up when the detected rise or fall timing corresponds to the timing for causing the position data count value to be counted up, and does not cause the position data count value to be counted up when the detected rise or fall timing does not correspond to the timing for causing the position data count value to be counted up.

Furthermore, the position data interpolation processor 27*d* controls the position data counter 27*da* so that the origin position of the stepping motor 22 has the position data count value "0", for example. Then, the position data interpolation processor 27*d* expresses the rotational position of the stepping motor 22 as a positive position data count value when the stepping motor 22 rotates in the positive direction with respect to the position data counter 27*da*, and expresses the rotational position of the stepping motor 22 as a negative position data count value when the stepping motor 22 rotates in the negative direction.

Note that, such processing performed by the position data interpolation processor 27*d* focuses on synchronization between the drive signal output from the motor controller 24 and the detection signal of the encoder 25 when the stepping motor 22 rotates. The number of microsteps per unit time of the drive signal output from the motor controller 24 (that is, the number of pulses of the microstep output pulse) is typically larger than the number of pulses per unit time of the detection signal of the encoder 25. Then, the rotational motion of the stepping motor 22 depends on the drive signal output from the motor controller 24, so that the pulse train of the microstep output pulse of the drive signal and the pulse train of the detection signal of the encoder 25 are nearly synchronized with each other usually. Thus, by using the number of microstep output pulses of the drive signal included between the pulses of the detection signal of the encoder 25 for interpolation between encoder count values of the encoder counter 27*a*, it is possible to generate position data of the transducer unit 21 with substantially higher resolution than a detection resolution of the encoder 25.

Note that, the position data generator 27 may generate an error signal when there is no pulse input of the detection signal of the encoder 25 for a predetermined time. This makes it possible to detect an abnormality in the stepping motor 22.

The memory 28 stores the conversion table 28*a* and the count processing setting table 28*b*.

The conversion table 28*a* is table data for converting the encoder count value indicated by the encoder counter 27*a* into a count value with the target resolution of the high-resolution position data as a reference (see FIG. 6 described later). For example, when the target resolution of the high-resolution position data is twice the actual detection resolution of the encoder 25, table data is stored in the conversion table 28*a* so that the encoder count value "1" is converted to "2", the encoder count value "2" is converted to "4", and the encoder count value "3" is converted to "6". By doing so, it is possible to interpolate count values (here, 1, 3, 5) between "0", "2", "4", and "6" with the number of microstep output pulses of the drive signal as a reference.

Note that, each time the target resolution of the high-resolution position data is designated by a user or the controller 11 of the main body 1, the conversion table 28*a* may be set on the basis of the detection resolution of the encoder 25 and the target resolution.

The count processing setting table 28*b* is table data that defines the timing for causing the position data count value to be counted up or counted down (see FIG. 7 described later). In the count processing setting table 28*b*, for example, position data count values and conditions for causing the position data count value to be counted up (hereinafter, collectively referred to as "count-up conditions of the position data counter 27*da*") are stored in association with each other.

The count-up conditions of the position data counter 27*da* are preferably set on the basis of the number of microsteps of the drive signal after the rise or fall of the pulse of the detection signal immediately before is detected. That is, the count processing setting table 28*b* defines how to interpolate the rotational position having a resolution that cannot be obtained from the detection signal of the encoder 25 from the microstep output pulse of the drive signal when the detection signal of the encoder 25 (that is, the encoder count value) is used as the true value of the rotational position of the stepping motor 22.

Note that, the count-up conditions of the position data counter 27*da* are set on the basis of the number of pulses of the detection signal output from the encoder 25 per unit amount of rotational displacement of the stepping motor 22, the number of microstep output pulses of the output drive signal output from the motor controller 24 for rotating the stepping motor 22 by a unit rotation angle, and the target resolution when the resolution of the encoder count value is increased.

Note that, the motor controller 24 and the position data generator 27 may be implemented by a digital arithmetic circuit including an Application Specific Integrated Circuit (ASIC), a Field-Programmable Gate Array (FPGA), or the like, or a part or all of them may be implemented by a Digital Signal Processor (DSP), a Central Processing Unit (CPU), a General-Purpose Graphics Processing Units (GPGPU), or the like performing arithmetic processing in accordance with a program.

[Operation Example of Position Data Generator]

Figure 5:
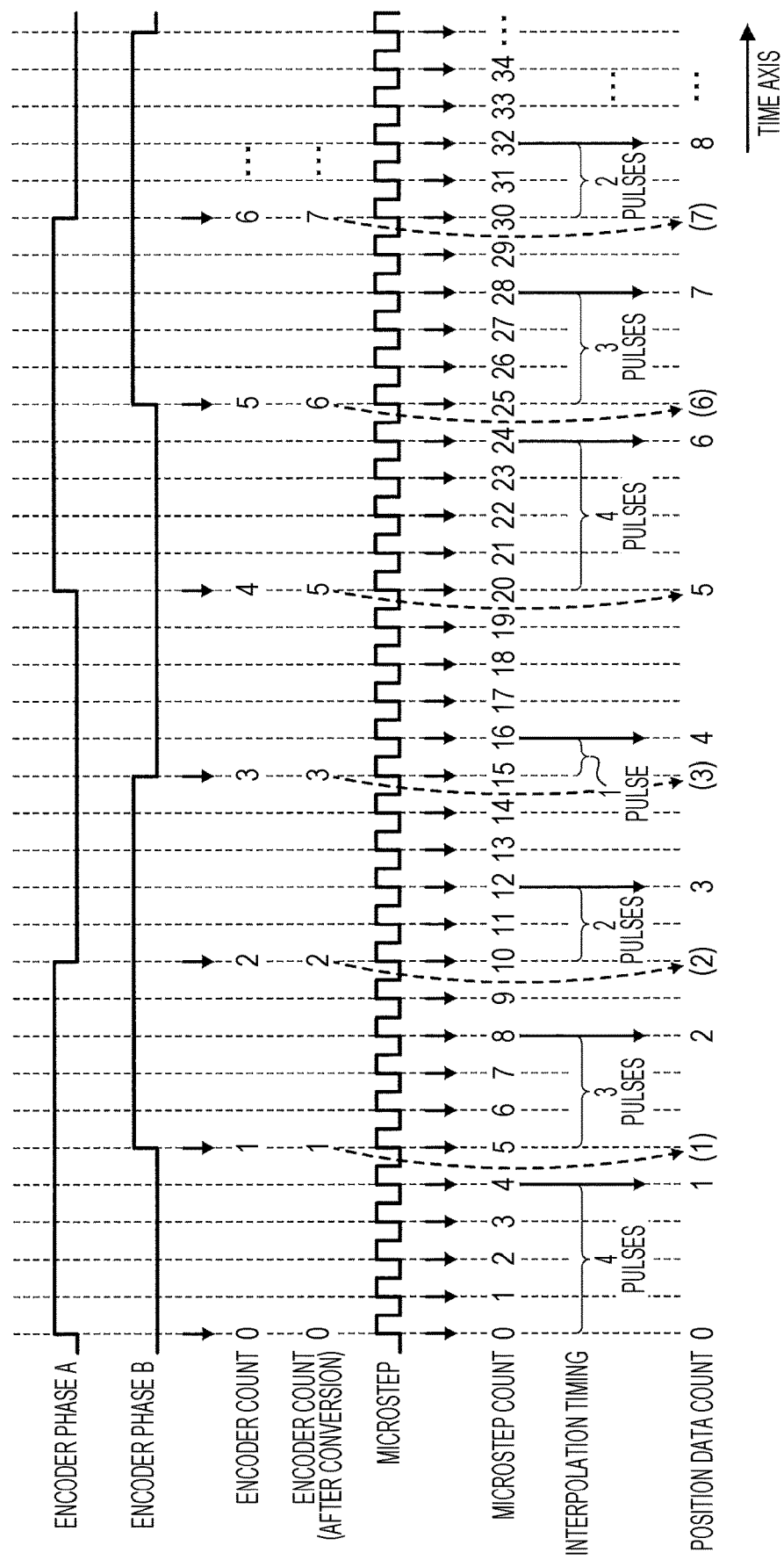
FIG. 5 is a diagram illustrating an example of position data generation processing by a position data generator.

FIG. 5 is a diagram illustrating an example of position data generation processing by the position data generator 27. FIG. 5 illustrates a time chart of the detection signal output from the encoder 25 and the drive signal output from the motor controller 24, and also illustrates the encoder count value, a microstep count value, the conversion encoder count value, and the position data count value that are generated by the detection signal and the drive signal.

FIG. 5 illustrates an example when high-resolution position data equivalent to 500 pulses/rotation is generated from the detection signal of the encoder 25 having a detection resolution of 400 pulses/rotation. Here, since the phase-A pulse and the phase-B pulse are used as the detection signals of the encoder 25, the detection resolution of 400 pulses/rotation corresponds to a detection resolution in units of a rotation angle 0.225° (=360°/(400×4)), and the detection resolution equivalent to 500 pulses/rotation corresponds to a detection resolution in units of rotation angle 0.18° (=360°/(500×4)). Furthermore, here, a case is assumed where the microstep of the drive signal is in units of 0.045° at the rotation angle of the stepping motor 22, and there are five microstep output pulses of the drive signal while the encoder counter 27a counts one.

In this case, to achieve the target resolution of the high-resolution position data, the position data generator 27 needs to detect the rotational positions of 0.18°, 0.36°, 0.54°, 0.72°, 0.9°, . . . when the stepping motor 22 rotates. However, from the pulse of the detection signal of the encoder 25, rotational positions that are integral multiples of 0.225° (for example, 0°, 0.9°, 1.8°) can be detected, but rotational positions that do not correspond to integral multiples of 0.225° (for example, 0.18°, 0.36°, 0.54°, 0.72°) cannot be detected. Thus, the position data generator 27 detects the rotational positions that do not correspond to the integral multiples of 0.225° by using the number of microstep output pulses of the drive signal.

FIG. 6 is a diagram illustrating an example of the conversion table 28a when the high-resolution position data equivalent to 500 pulses/rotation is generated from the detection signal of the encoder 25 having the detection resolution of 400 pulses/rotation.

In the conversion table 28a of FIG. 6, a value obtained by multiplying the encoder count value by 1.25 (=500 pulses/rotation÷400 pulses/rotation) and rounding down after the decimal point is set as the conversion encoder count value. Note that, in FIG. 6, a case where the encoder count value is "0" corresponds to a case where the stepping motor 22 (transducer unit 21) exists at the origin position.

Here, when the encoder count value is a multiple of 4 (that is, the conversion encoder count value is a multiple of 5), the conversion encoder count value is a true value that matches the actual rotational position of the stepping motor 22, but when the encoder count value is other than a multiple of 4, the conversion encoder count value is not a true value that matches the actual rotational position of the stepping motor 22. Specifically, when the encoder count value is other than a multiple of 4, the conversion encoder count value indicates a rotational position smaller than the actual rotational position of the stepping motor 22 by an amount rounded down after the decimal point when the target resolution is used as a reference. For that reason, the position data generator 27 specifies the rotational position of the stepping motor 22 when the encoder count value is other than a multiple of 4 with the number of microstep output pulses of the drive signal as a reference.

FIG. 7 is a diagram illustrating an example of the count processing setting table 28b when the high-resolution position data equivalent to 500 pulses/rotation is generated from the detection signal of the encoder 25 having the detection resolution of 400 pulses/rotation.

In the count processing setting table 28b of FIG. 7, with a period between timings at which position data count values are multiple of 5 as one period, the conditions are set for causing the position data count value to be counted up when the position data count values are 5m (m represents an integer, the same applies hereinafter), 5m+1, 5m+2, 5m+3, and 5m+4. A timing at which the position data count value is a multiple of 5 is a timing at which the encoder count value is a multiple of 4, and a count value indicated by the conversion encoder count value corresponds to a timing at which a true value is indicated in the target resolution of the high-resolution position data.

In other words, in the count processing setting table 28b of FIG. 7, the count-up conditions are set so that the rotational position of the stepping motor 22 that cannot be detected from the rise or fall timing of the pulse of the detection signal of the encoder 25, for example, the rotational positions of 0.18°, 0.36°, 0.54°, 0.72°, . . . , are detected from the number of microstep output pulses of the drive signal. Note that, in the count processing setting table 28b in FIG. 7, from a viewpoint of improving detection accuracy, the count-up conditions are set with the number of input pulses of the microstep output pulse of the drive signal from the rise or fall timing of the pulse of the detection signal of the encoder 25 immediately before as a reference.

For example, when the position data count value is 5m (the rotation angle of the stepping motor 22 is 0.18°×5m), it is necessary to cause the position data count value to be counted up when the stepping motor 22 rotates 0.18° after the conversion encoder count value immediately before (that is, 5m) is reflected. For that reason, the condition is set so that the position data count value is counted up when four microstep output pulses of the drive signal are input (0.045°×4=0.18°).

Furthermore, when the position data count value is 5m+1 (the rotation angle of the stepping motor 22 is 0.18°×(5m+1)), it is necessary to count up faster than when the position data count value is 5m by the amount (here, 0.25 after the decimal point) rounded down when the encoder count value is calculated, after the conversion encoder count value immediately before (that is, 5m+1) is reflected. For that reason, the condition is set so that, to cause the position data count value to be counted up when the stepping motor 22 rotates 0.135° after the conversion encoder count value immediately before is reflected, the position data count value is counted up when three microstep output pulses of the drive signal are input (0.045°×3=0.135°).

Furthermore, when the position data count value is 5m+2 (the rotation angle of the stepping motor 22 is 0.18°×(5m+2)), the position data count value is counted up when two microstep output pulses of the drive signal are input (0.045°×2=0.09°) after the conversion encoder count value immediately before is reflected.

Furthermore, when the position data count value is 5m+3 (the rotation angle of the stepping motor 22 is 0.18°×(5m+3)), the position data count value is counted up when one microstep output pulse of the drive signal is input (0.045°×1=0.045°) after the conversion encoder count value immediately before is reflected.

Furthermore, when the position data count value is 5m+4 (the rotation angle of the stepping motor 22 is 0.18°×(5m+4)), a timing at which the pulse of the detection signal of the encoder 25 is input matches a timing of the target resolution of the high-resolution position data, so that the conversion encoder count value is directly reflected in the position data count value when the pulse of the detection signal of the encoder 25 is input.

Signal processing of FIG. 5 is executed on the basis of the conversion table 28a of FIG. 6 and the count processing setting table 28b of FIG. 7. In FIG. 5, it can be seen that the encoder count value of the 400 pulses/rotation encoder is converted into a count value equivalent to 500 pulses/rotation each time the value is counted up. Then, the conversion encoder count value is sequentially reflected in the position data count value of the position data counter 27*da*. Furthermore, the position data count value of the position data counter 27*da* is counted up each time a predetermined number of microstep output pulses of the drive signal are input after the conversion encoder count value immediately before is reflected in accordance with the count processing setting table 28*b*.

Figure 8:
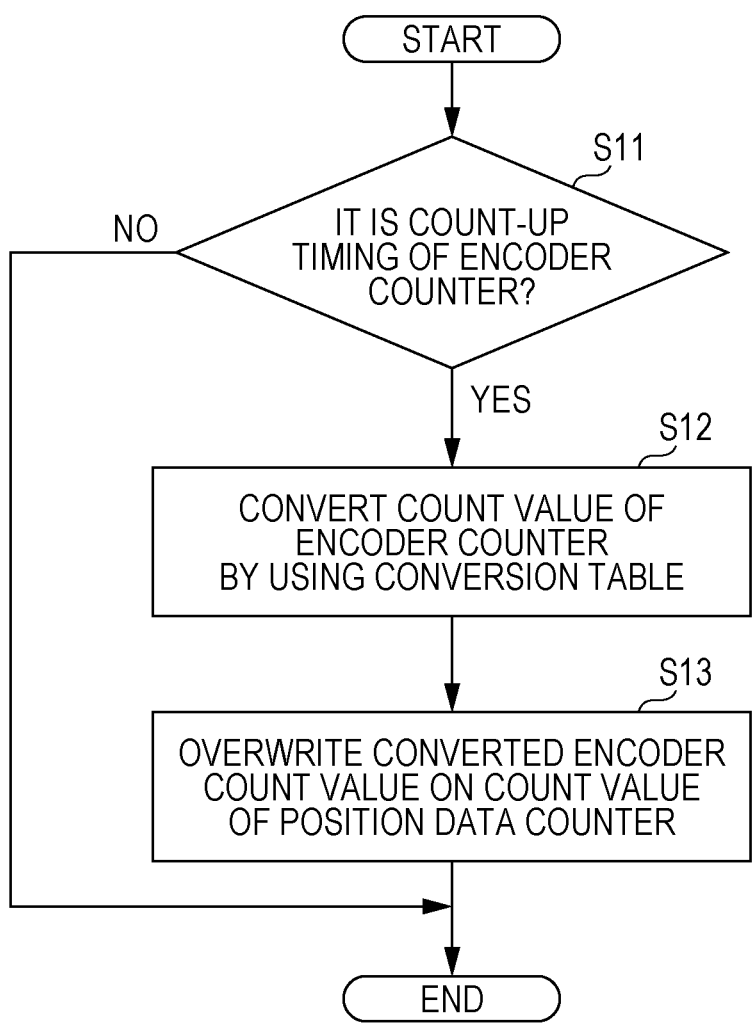
FIG. 8 is a flowchart illustrating an example of high-resolution position data generation processing by a position data converter and a position data interpolation processor.
Figure 9:
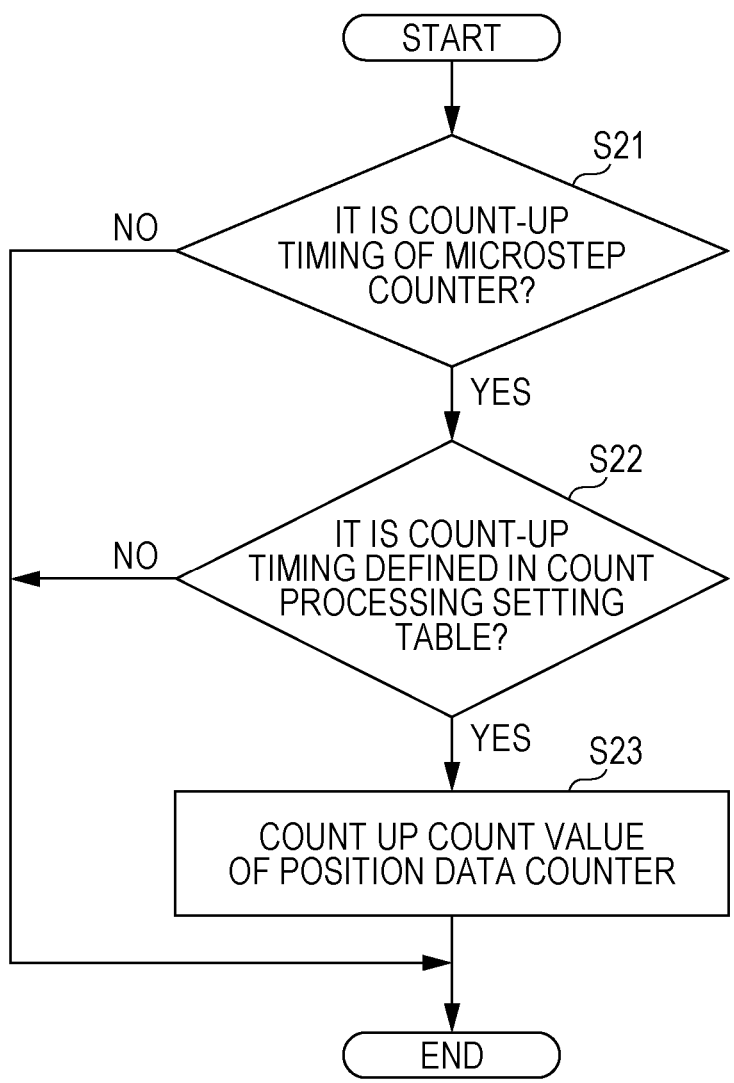
FIG. 9 is a flowchart illustrating an example of the high-resolution position data generation processing by the position data converter and the position data interpolation processor.

FIGS. 8 and 9 are flowcharts illustrating an example of high-resolution position data generation processing by the position data converter 27*b* and the position data interpolation processor 27*d*. The processing of the flowcharts of FIGS. 8 and 9 is processing executed by the position data interpolation processor 27*d* in accordance with a computer program at predetermined time intervals. Note that, the processing of the flowchart of FIG. 8 and the processing of the flowchart of FIG. 9 may be executed by a single processor in a time-division manner, or may be executed in parallel by a plurality of processors.

First, the processing of the flowchart of FIG. 8 will be described.

In step S11, the position data converter 27*b* determines whether or not it is a count-up timing of the encoder counter 27*a*. Then, when it is the count-up timing of the encoder counter 27*a* (S11: YES), the position data converter 27*b* proceeds to perform processing in step S12, and when it is not the count-up timing of the encoder counter 27*a* (S11: NO), the position data converter 27*b* ends the processing of the flowchart of FIG. 8 without executing any processing in particular.

In step S12, the position data converter 27*b* converts the encoder count value of the encoder counter 27*a* by using the conversion table 28*a*.

In step S13, the position data converter 27*b* outputs the encoder count value converted in step S12 to the position data interpolation processor 27*d*. Then, the position data interpolation processor 27*d* overwrites the encoder count value (conversion encoder count value) onto the position data count value of the position data counter 27*da* each time the encoder count value output from the position data converter 27*b* is counted up.

The position data interpolation processor 27*d* executes the processing of the flowchart of FIG. 8 typically at a time interval (for example, 25 nsec interval) shorter than the time width of the unit microstep of the microstep output pulse.

Next, the processing of the flowchart of FIG. 9 will be described.

In step S21, the position data interpolation processor 27*d* determines whether or not it is a count-up timing of the microstep counter 27*c*. Then, when it is the count-up timing of the microstep counter 27*c* (S21: YES), the position data interpolation processor 27*d* proceeds to perform processing in step S22, and when it is not the count-up timing of the microstep counter 27*c* (S21: NO), the position data interpolation processor 27*d* ends the processing of the flowchart of FIG. 9 without executing any processing in particular.

In step S22, the position data interpolation processor 27*d* determines whether or not it is a timing to count up the position data counter 27*da* by referring to the count processing setting table 28*b*. Then, when it is the timing to count up the position data counter 27*da* (S22: YES), the position data interpolation processor 27*d* proceeds to perform processing in step S23, and when it is not the timing to count up the position data counter 27*da* (S22: NO), the position data interpolation processor 27*d* ends the processing of the flowchart of FIG. 9 without executing any processing in particular.

In step S23, the position data interpolation processor 27*d* counts up the position data count value of the position data counter 27*da*. Then, the position data interpolation processor 27*d* outputs the position data count value of the position data counter 27*da* to the controller 11 of the main body 1.

The position data interpolation processor 27*d* executes the processing of the flowchart of FIG. 9 typically at a time interval (for example, 25 nsec interval) shorter than the time width of the unit microstep of the microstep output pulse.

Note that, in the above, the description has been given of the high-resolution position data generation processing when the stepping motor 22 rotates in the positive direction with respect to the origin position, but the same applies to the high-resolution position data generation processing when the stepping motor 22 rotates in the negative direction with respect to the origin position. When the stepping motor 22 rotates in the negative direction with respect to the origin position, the position data interpolation processor 27*d* expresses the rotational position of the stepping motor 22 as, for example, a negative position data count value.

Effects

As described above, with the ultrasonic diagnostic apparatus A according to the present embodiment, it is possible to acquire the position data of the transducer unit 21 with higher resolution than the detection resolution of the encoder 25 without increasing the resolution itself of the encoder 25 (that is, using a small encoder). As a result, for example, the swing position of the transducer unit 21 can be grasped with higher accuracy, and a higher definition ultrasonic image can be generated.

In particular, the ultrasonic diagnostic apparatus A according to the present embodiment specifies the swing position of the unit 21 by using the detection signal of the encoder 25 and the drive signal output from the motor controller 24, both of which indicates current rotational behavior of the stepping motor 22, so that the swing position of the transducer unit 21 can be specified with high accuracy even when the stepping motor 22 accelerates or decelerates.

Furthermore, in particular, in the ultrasonic diagnostic apparatus A according to the present embodiment, the timing between the pulses of the detection signal is interpolated on the basis of the number of microsteps of the drive signal after the rise or fall of the pulse of the detection signal of the encoder 25 immediately before is detected. That is, in the ultrasonic diagnostic apparatus A according to the present embodiment, the detection signal of the encoder 25 is used as a true value for specifying the rotational position of the stepping motor 22 (that is, the position of the transducer unit 21), and the number of microstep output pulses of the drive signal output from the motor controller 24 is referred to only for interpolating the value (that is, the position of the transducer unit 21) of the resolution that cannot be obtained from the detection signal of the encoder 25. As a result, even when the drive signal is delayed due to an increase in a rotational load of the transducer unit 21, the rotational position of the stepping motor 22 can be appropriately captured.

Furthermore, in particular, in the ultrasonic diagnostic apparatus A according to the present embodiment, the count-up processing depending on the position data count value of the position data counter 27*da* is executed by using the count processing setting table 28*b*. As a result, the present invention can be applied without being restricted by a relationship between a mechanical angle (that is, a step angle) of the stepping motor 22 and a slit interval of the encoder 25. That is, as a result, the present invention can be applied without depending on the types of the stepping motor 22 and the encoder 25 built in the ultrasonic probe 2, which is useful from a practical viewpoint.

(Modification 1)

Figure 10:
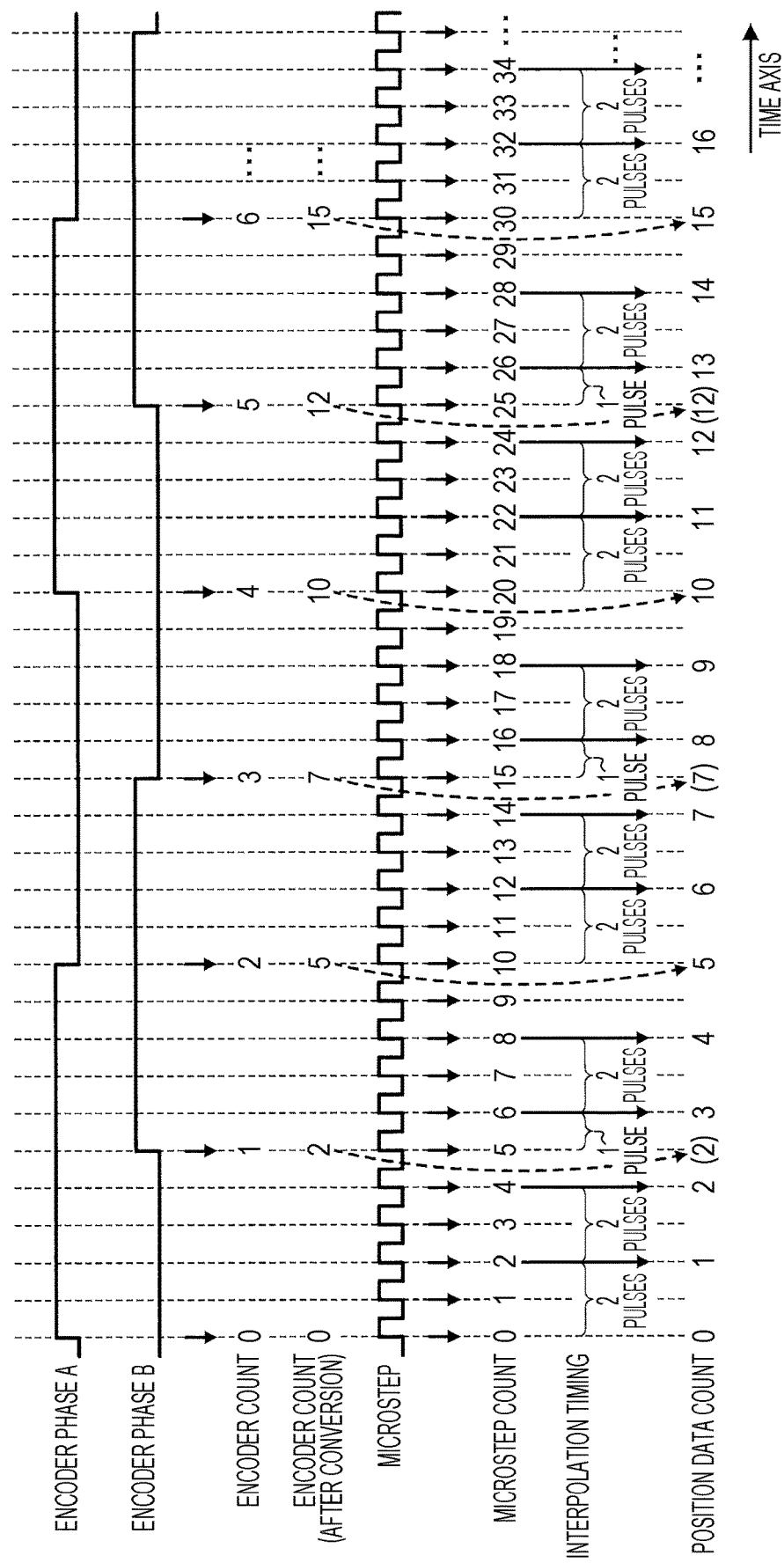
FIG. 10 is a diagram illustrating another example of the position data generation processing by the position data generator.

FIG. 10 is a diagram illustrating another example of the position data generation processing by the position data generator 27. FIG. 10 illustrates an example when high-resolution position data equivalent to 1000 pulses/rotation is generated from the detection signal of the encoder 25 having the detection resolution of 400 pulses/rotation. Note that, a detection resolution equivalent to 1000 pulses/rotation corresponds to a detection resolution in units of rotation angle 0.09° (=360°/(1000×4)).

FIG. 11 is a diagram illustrating an example of the conversion table 28a when the high-resolution position data equivalent to 1000 pulses/rotation is generated from the detection signal of the encoder 25 having the detection resolution of 400 pulses/rotation. In the conversion table 28a of FIG. 11, a value obtained by multiplying the encoder count value by 2.5 (=1000 pulses/rotation÷400 pulses/rotation) and rounding down after the decimal point is set as the conversion encoder count value.

FIG. 12 is a diagram illustrating an example of the count processing setting table 28b when the high-resolution position data equivalent to 1000 pulses/rotation is generated from the detection signal of the encoder 25 having the detection resolution of 400 pulses/rotation. In the count processing setting table 28b of FIG. 12, with a period between timings at which position data count values are multiple of 10 as one period, the conditions are set for causing the position data count value to be counted up or counted down when the position data count values are 10m, 10m+1, 10m+2, 10m+3, 10m+4, 10m+5, 10m+6, 10m+7, 10m+8, and 10m+9.

In the count processing setting table 28b of FIG. 12, conditions are set so that the rotational position of the stepping motor 22 that cannot be detected from the rise or fall timing of the pulse of the detection signal of the encoder 25, for example, the rotational positions of 0.09°, 0.18°, 0.27°, 0.36°, 0.54°, 0.63°, 0.72°, 0.81°, . . . , are detected from the number of microstep output pulses of the drive signal.

Furthermore, also in the count processing setting table 28b of FIG. 12, from the viewpoint of improving the detection accuracy, the count-up conditions are set with the number of input pulses of the microstep output pulse of the drive signal from the rise or fall timing of the pulse of the detection signal of the encoder 25 immediately before as a reference.

As described above, with the ultrasonic diagnostic apparatus A according to the above embodiment, it is possible to change the target resolution of the high-resolution position data only by changing the conversion table 28a and the count processing setting table 28b.

(Modification 2)

Figure 13:
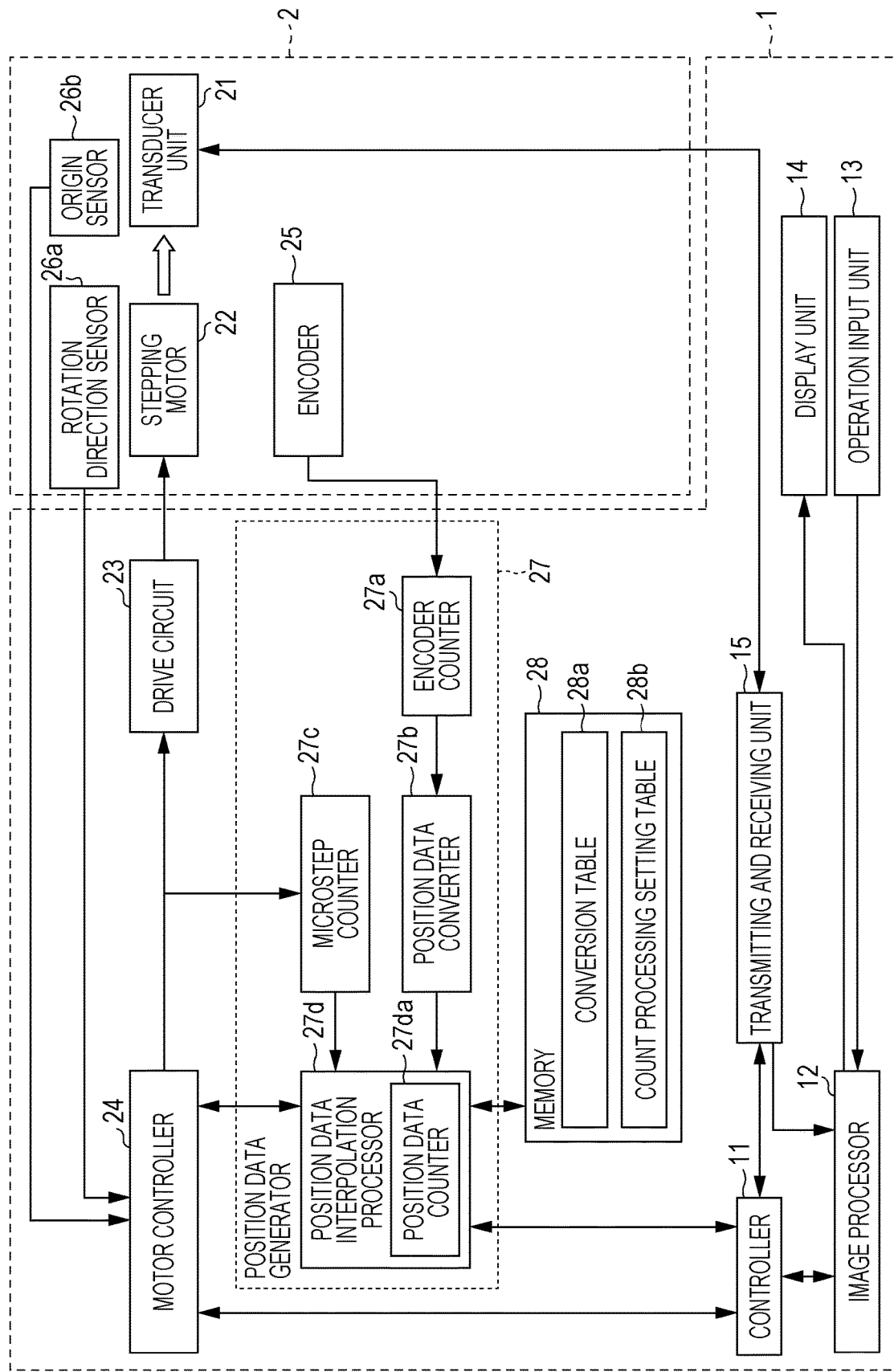
FIG. 13 is a diagram illustrating a configuration of an ultrasonic diagnostic apparatus according to Modification 2.

FIG. 13 is a diagram illustrating a configuration of the ultrasonic diagnostic apparatus A according to Modification 2.

The ultrasonic diagnostic apparatus A according to Modification 2 is different from the ultrasonic diagnostic apparatus A according to the above embodiment in that the drive circuit 23, the motor controller 24, the position data generator 27, and the memory 28 are housed in a housing of the main body 1 of the ultrasonic diagnostic apparatus A, not in the housing of the ultrasonic probe 2. Note that, the function of each component is the same as the function described in the above embodiment.

In the ultrasonic diagnostic apparatus A according to Modification 2, it is possible to complete the signal processing inside the ultrasonic diagnostic apparatus main body 1 when executing ultrasonography. As a result, it is possible to save a trouble of data transmission between the ultrasonic diagnostic apparatus main body 1 and the ultrasonic probe 2. Furthermore, this makes it possible to reduce the size of the ultrasonic probe 2.

Other Embodiments

The present invention is not limited to the above embodiment, and various modified modes are conceivable.

In the above embodiment, two examples, the target resolutions equivalent to 500 pulses/rotation and 1000 pulses/rotation, have been described as the target resolutions when generating the high-resolution position data from the detection signal of the encoder 25 having the detection resolution of 400 pulses/rotation. The target resolution of the high-resolution position data only needs to be set on the basis of, for example, the number of pulses of the detection signal output from the encoder 25 per unit amount of rotational displacement of the stepping motor 22, and the number of microstep output pulses of the drive signal output from the motor controller 24 for rotating the stepping motor 22 by the unit amount of rotational displacement. For example, the target resolution of the high-resolution position data is preferably a value in which the rotation angle unit of the target resolution is an integral multiple of the rotation angle unit of the microstep output pulse of the drive signal, and the rotational position that can be detected by the encoder 25 appears each time within 10 units of the rotation angle unit of the target resolution.

Furthermore, in the above embodiment, as an example of the position data generator 27, a mode has been described in which when the rise of the pulse of the detection signal of the encoder 25 is detected, all the encoder count values output from the encoder counter 27a are reflected in the position data counter 27da. However, a configuration may be adopted in which when the position data generator 27 converts the encoder count value into a count value with the target resolution of the high-resolution position data as a reference, the position data generator 27 does not reflect an encoder count value including a fraction, in the high-resolution position data (that is, does not overwrite the encoder count value onto the position data counter 27da). However, even with such a configuration, it is preferable that the position data generator 27 determines the count-up conditions of the position data counter 27da with the timing of the rise of the pulse of the detection signal of the encoder 25 immediately before as a reference.

Furthermore, in the above embodiment, as an example of the count processing setting table 28b, a data table has been described in which the position data count value and the condition for causing the position data count value to be counted up are associated with each other. However, in the count processing setting table 28b, the condition for causing the position data count value to be counted up may be set with the current encoder count value or a converted value of the current encoder count value as a reference, instead of the position data count value.

Furthermore, in the above embodiment, as an example of the ultrasonic probe 2 applied to the ultrasonic diagnostic apparatus A, a probe has been described of a type in which the transducer unit 21 is swung in an arc shape. However, the ultrasonic probe 2 applied to the ultrasonic diagnostic apparatus A according to the present invention can be applied to other mechanical ultrasonic probes such as a linear swing type (a type in which the transducer unit is swung linearly in parallel).

Furthermore, in the above embodiment, a mode has been described in which an optical encoder is used as an example of the encoder 25. However, in the present invention, the encoder 25 may be a magnetic or mechanical encoder.

With the ultrasonic diagnostic apparatus according to the present disclosure, it is possible to increase the resolution of the position information of the transducer unit without changing the detection resolution itself of the encoder.

Although embodiments of the present invention have been described and illustrated in detail, the disclosed embodiments are made for purposes of illustration and example only and not limitation. The scope of the present invention should be interpreted by terms of the appended claims. Technologies described in the claims include various modifications and changes of the specific examples exemplified above.

What is claimed is:

1. An ultrasonic diagnostic apparatus that generates an ultrasonic image of a subject by using an ultrasonic probe, the ultrasonic diagnostic apparatus comprising:
    a transducer unit that is arranged in the ultrasonic probe and performs transmission and reception of ultrasonic waves;
    a stepping motor that is arranged in the ultrasonic probe and moves the transducer unit;
    a motor controller that sends a drive signal of a microstep drive method to the stepping motor;
    an encoder that is arranged in the ultrasonic probe, detects rotational motion of the stepping motor, and generates a detection signal having a pulse train shape depending on an amount of rotational displacement per unit time of the stepping motor; and
    a digital arithmetic circuit that detects each rise or fall of a pulse of the detection signal, detects each rise or fall of a microstep of the drive signal when the stepping motor rotates to obtain a number of microsteps of the drive signal, and generates high-resolution position data in which a resolution of first position data of the transducer unit obtained from the detection signal is increased by interpolating the first position data of the transducer unit at a timing between the detections of each rise or fall of the pulse of the detection signal with the number of microsteps of the drive signal as a reference.

2. The ultrasonic diagnostic apparatus according to claim 1, wherein
    the digital arithmetic circuit
    interpolates the first position data of the transducer unit at the timing between the detections of the rise or fall of the pulse of the detection signal on a basis of the number of microsteps of the drive signal immediately after detected rise the microsteps of the drive signal, wherein the number of microsteps of the drive signal constitutes a number of microsteps of the drive signal or fall of the pulse of the detection signal.

3. The ultrasonic diagnostic apparatus according to claim 1, wherein
    the digital arithmetic circuit includes:
    an encoder counter that receives the detection signal as an input and performs count processing for each rise or fall of the pulse of the detection signal;
    a microstep counter that receives the drive signal as an input and performs count processing for each rise or fall of the microstep of the drive signal to output the number of microsteps of the drive signal;
    a position data converter that converts an encoder count value output from the encoder counter into a count value with a target resolution of the high-resolution position data as a reference by referring to a predetermined conversion table; and
    a position data interpolation processor that generates the high-resolution position data on a basis of the encoder count value after conversion and the number of microsteps of the drive signal output from the microstep counter.

4. The ultrasonic diagnostic apparatus according to claim 1, wherein
    the digital arithmetic circuit generates an error signal when there is no pulse input of the detection signal for a predetermined time.

5. The ultrasonic diagnostic apparatus according to claim 1, further comprising
    an image processor that generates the ultrasonic image on a basis of an ultrasonic echo acquired by the transducer unit and the high-resolution position data.

6. The ultrasonic diagnostic apparatus according to claim 1, wherein
    the ultrasonic probe is a 4D probe enabled to reciprocate the transducer unit in a direction orthogonal to an arrangement direction of transducers of the transducer unit.

7. The ultrasonic diagnostic apparatus according to claim 1, wherein
    the motor controller is arranged in the ultrasonic probe.

8. The ultrasonic diagnostic apparatus according to claim 1, wherein
    the motor controller is arranged in a main body of the ultrasonic diagnostic apparatus.

9. The ultrasonic diagnostic apparatus according to claim 3, wherein
    the position data interpolation processor
    includes a position data counter that generates a count value representing the high-resolution position data,
    causes the position data counter to perform counting up or counting down as the number of microsteps of the drive signal reaches a predetermined number, and
    overwrites and updates the count value of the position data counter with the encoder count value after the conversion, along with the counting up or counting down of the encoder count value after the conversion.

10. The ultrasonic diagnostic apparatus according to claim 9, wherein
    the position data interpolation processor,
    when each rise or fall of the microstep of the drive signal is detected, refers to a predetermined count processing setting table, in which a predetermined timing at which the count value of the position data counter is counted up or counted down is defined, to determine whether or not a detected rise or fall timing at which each rise or fall of the microstep of the drive signal is detected corresponds to the predetermined timing,
    causes the count value of the position data counter to be counted up or counted down when the detected rise or fall timing corresponds to the predetermined timing, and does not cause the count value of the position data counter to be counted up or counted down when the detected rise or fall timing does not correspond to the predetermined timing.

11. The ultrasonic diagnostic apparatus according to claim 5, wherein
the ultrasonic image is a 3D image formed by synthesizing tomographic images of the subject acquired when the transducer unit is in respective rotational positions.

12. An ultrasonic probe of an ultrasonic diagnostic apparatus that generates an ultrasonic image of a subject, the ultrasonic probe comprising:
a transducer unit that performs transmission and reception of ultrasonic waves;
a stepping motor that moves the transducer unit;
a motor controller that sends a drive signal of a microstep drive method to the stepping motor;
an encoder that detects rotational motion of the stepping motor, and generates a detection signal having a pulse train shape depending on an amount of rotational displacement per unit time of the stepping motor; and
a digital arithmetic circuit that detects each rise or fall of a pulse of the detection signal, detects each rise or fall of a microstep of the drive signal when the stepping motor rotates to obtain a number of microsteps of the drive signal, and generates high-resolution position data in which a resolution of first position data of the transducer unit obtained from the detection signal is increased by using the first position data obtained from the detection signal and interpolating the first position data of the transducer unit at a timing between the detections of each rise or fall of the pulse of the detection signal with the number of microsteps of the drive signal as a reference.

\* \* \* \* \*